United States Patent [19]

Mizoguchi

[11] Patent Number: 5,264,622
[45] Date of Patent: Nov. 23, 1993

[54] WATER-SOLUBLE METHYLENEBIS(DIALKYLANILINE) DERIVATIVES AND APPLICATION THEREOF

[75] Inventor: Makoto Mizoguchi, Kumamoto, Japan

[73] Assignee: Dojindo Laboratories, Japan

[21] Appl. No.: 994,297

[22] Filed: Dec. 21, 1992

[30] Foreign Application Priority Data

Jan. 28, 1992 [JP] Japan ................... 4-054477

[51] Int. Cl.$^5$ .................. C07C 309/24; G01N 33/50
[52] U.S. Cl. ........................ 562/43; 562/44; 435/28; 436/112
[58] Field of Search ............. 562/43, 44; 435/28; 436/112

[56] References Cited

FOREIGN PATENT DOCUMENTS 56-99454 8/1981 Japan .
57-64660 4/1982 Japan .

OTHER PUBLICATIONS

Shiga et al, Chemical Abstracts, vol. 100 (1983) 19880s.

Dojin Kaguhu; Chemical Abstracts, vol. 101 (1984) 68922m.

*Primary Examiner*—Richard L. Raymond
*Attorney, Agent, or Firm*—Rosenman & Colin

[57] ABSTRACT

Novel water-soluble methylenebis(dialkylaniline) derivatives of the following general formula and salts thereof are disclosed. They are useful as dye-forming substances in quantitative determination of peroxides in the copresence of peroxidase or the like.

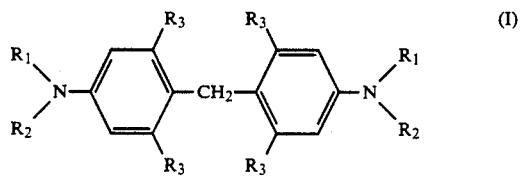

In the formula, $R_1$ is hydrogen or a substituent selected from lower alkyl and $C_{2-3}$ sulfoalkyl or hydroxysulfoalkyl; $R_2$ is $C_{2-3}$ sulfoalkyl or hydroxysulfoalkyl; and $R_3$ is lower alkyl.

9 Claims, 1 Drawing Sheet

WATER-SOLUBLE METHYLENEBIS(DIALKYLANILINE) DERIVATIVES AND APPLICATION THEREOF

BACKGROUND OF THE INVENTION

The present invention relates to novel water-soluble methylenebis(dialkylaniline) derivatives and salts thereof. The invention also relates to a composition for the quantitative determination of peroxides containing the present invention compounds as a dye-forming substance.

DETAILED DESCRIPTION OF THE INVENTION

The present invention relates to water-soluble methylenebis(dialkylaniline) derivatives represented by the general formula (I) as given in claim 1 and salt thereof (hereinafter, referred to as "the present invention compound") and also relates to a composition for quantitative determination of peroxides containing the present invention compound as a dye-forming substance.

All of the present invention compounds are new having not been disclosed in prior art literatures and are useful as dye-forming substance in quantitative determination of peroxides in the copresence of peroxidase or a substance having the same catalytic action.

Because of the substrate specificities of enzymes, clinical test method using an enzyme reagent is a very selective method of analysis. Since said method is capable of conducting quantitative determination of various components in biological system easily without an interference from complicated biomatrix, it is now an important analytical means inevitable for clinical chemical analyses with the spread of automated analytical machines. Particularly noticeable one in the analysis of components in biological system using enzymatic analytical method is a system wherein hydrogen peroxide is generated by an enzymatic reaction. Thus, various oxidases which generate hydrogen peroxide as a result of selective action on components in biological system have been widely used and, at present, oxidases corresponding to nearly all components in biological system are known. Accordingly, it is now possible to conduct a quantitative determination of desired components in biological system by quantitative determination of the resulting hydrogen peroxide provided that a proper oxidase is available.

The most common means for quantitative determination of hydrogen peroxide generated by such a mechanism is that hydrogen donor is condensed with a coupler (such as 4-aminoantipyrine; hereinafter, referred to as 4-AA) by oxidation using hydrogen peroxide in the presence of peroxidase (hereinafter, referred to as POD) and coloration of the condensate is measured by means of absorptiometry. Examples of the methods reported are given in Table 1.

TABLE 1

Quantitative Determination of Hydrogen Peroxide using POD

| Coupler | Hydrogen Donor | Formed Chromogen $\lambda_{max}$, nm |
|---|---|---|
| 4-AA | Phenol | 505 |
| 4-AA | N,N-Dimethylaniline | 550 |
| 4-AA | 4-Chlorophenol | 505 |
| 4-AA | 2,4,6-Tribromophenol | 492 |

TABLE 1-continued

Quantitative Determination of Hydrogen Peroxide using POD

| Coupler | Hydrogen Donor | Formed Chromogen $\lambda_{max}$, nm |
|---|---|---|
| 4-AA | N-Ethyl-N-sulfopropylaniline | 561 |
| 4-AA | N-Ethyl-N-(2-hydroxy-3-sulfopropyl)-m-toluidine | 555 |

It is an essential requirement in clinical chemical tests to make the detection sensivitity higher because of the use of blood which is a precious sample and also because of measurment of components in very small quantity. In view of that, there has been a demand for reagents having higher sensitivity than those of the hydrogen donators as given in the above Table 1. Moreover, most of those known dye-forming substances absorb at wavelengths of 500–600 nm while the absorption caused by homolysis and bilirubin contained in body liquid is within a wide range from ultraviolet region to around 530 nm whereby there is a possibility of resulting in a positive error in the measurement and, consequently, there has been a demand for hydrogen donors which are colored in higher wavelength region.

The present inventor has conducted extensive studies for finding dye-forming substances which produce dyes with wavelength of 600 nm or longer and particularly with high solubility in water and found the present invention compound represented by the already-given general formula (I). It has also been found that, unlike in the conventional methods (cf. Japanese Laid Open Application 56/99454 and 57/64660), the present invention compound does not require couplers but is colored only by enzyme and hydrogen peroxide. For example, when the present invention compound is oxidized with peroxidase and hydrogen peroxide, blue dye of the following general formula (II) is produced quantitatively whereupon satisfactory color stability can be sustained. Thus, the present invention has been achieved.

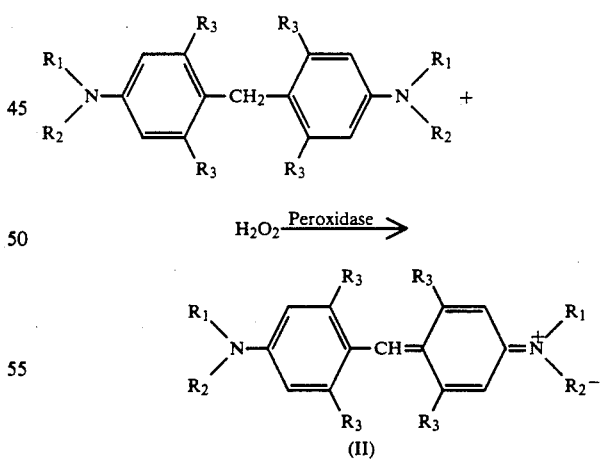

(II)

The characteristic feature of the present invention that it does not need couplers is a very useful advantage in terms of simplification of measuring operations by automatic analytic machines which are now in a stage of continuing progress. In addition, when the present invention compound is dissolved in a buffer of PH 5.5 followed by adding peroxidase and hydrogen peroxide, a dye with molar extinction coefficient of $4.0 \times 10^4$ to $5.0 \times 10^4$ ($1.mol^{-1}.cm^{-1}$) at the maximum absorption wavelength is produced while, when the measurement is conducted under the same conditions using phenol and 4-aminoantipyrine, the molar extinction coefficient at the maximum absorption wavelength is only about $5.0 \times 10^3$. Consequently quantitative determination method of hydrogen peroxide using the present invention compound is with very high sensitivity.

The compound of the general formula (I) can be synthesized by the reaction of the compound of the following general formula (III)

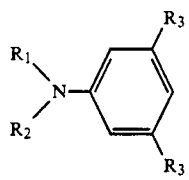

[wherein $R^1$, $R^2$ and $R^3$ are the same as those defined already for (I)] with formalin. Specific examples of the present invention compound of the general formula (I) prepared as such are given in Table 2; and melting points and elementary analyses of the compound as well as the maximum absorption wavelengths of the oxidized dyes obtained by treating with hydrogen peroxide at pH 5.5 are given in Table 3.

TABLE 2

| Compound | $R_1$ | $R_2$ | $R_3$ |
|---|---|---|---|
| A | $C_2H_5$ | $C_2H_4SO_3Na$ | $CH_3$ |
| B | H | $C_3H_6SO_3Na$ | $CH_3$ |
| C | H | $C_3H_6SO_3Na$ | $C_2H_5$ |
| D | $CH_3$ | $C_3H_6SO_3Na$ | $CH_3$ |
| E | $CH_3$ | $C_3H_6SO_3Na$ | $C_2H_5$ |
| F | $C_2H_5$ | $C_3H_6SO_3Na$ | $CH_3$ |
| G | $C_2H_5$ | $C_3H_6SO_3Na$ | $C_2H_5$ |
| H | $C_3H_7$ | $C_3H_6SO_3Na$ | $CH_3$ |
| I | $C_3H_7$ | $C_3H_6SO_3Na$ | $C_2H_5$ |
| J | $CH_3$ | $C_3H_5(OH)SO_3Na$ | $CH_3$ |
| K | $CH_3$ | $C_3H_5(OH)SO_3Na$ | $C_2H_5$ |
| L | $C_2H_5$ | $C_3H_5(OH)SO_3Na$ | $CH_3$ |
| M | $C_2H_5$ | $C_3H_5(OH)SO_3Na$ | $C_2H_5$ |
| N | $C_2H_5$ | $C_3H_6SO_3Na$ | $C_3H_7$ |
| O | $C_4H_9$ | $C_3H_6SO_3Na$ | $C_2H_5$ |

TABLE 3

| Compound | Melting Point (°C.) | Molecular Formula | Elementary Analysis (%) C (theoretical value) (calculated value) | H | N | Absorption Wavelength $\lambda_{max}$ (nm) |
|---|---|---|---|---|---|---|
| A | 220–223 (decompn) | $C_{25}H_{36}N_2O_6S_2Na_2$ | 52.61 / 52.32 | 6.35 / 6.46 | 4.91 / 4.69 | 633 |
| B | 198–210 (decompn) | $C_{23}H_{32}N_2O_6S_2Na_2$ | 50.01 / 50.26 | 5.94 / 6.00 | 5.16 / 5.19 | 625 |
| C | 201–213 (decompn) | $C_{27}H_{40}N_2O_6S_2Na_2$ | 54.16 / 54.22 | 6.73 / 6.49 | 4.67 / 4.59 | 629 |
| D | 222–236 (decompn) | $C_{25}H_{36}N_2O_6S_2Na_2$ | 52.61 / 52.55 | 6.35 / 6.29 | 4.90 / 4.77 | 635 |
| E | 232–244 (decompn) | $C_{29}H_{44}N_2O_6S_2Na_2 \cdot H_2O$ | 54.02 / 54.00 | 7.19 / 7.09 | 4.34 / 4.30 | 644 |
| F | 225–245 (decompn) | $C_{27}H_{40}N_2O_6S_2Na_2$ | 54.16 / 54.25 | 6.73 / 6.80 | 4.67 / 4.60 | 647 |
| G | 232–244 (decompn) | $C_{31}H_{48}N_2O_6S_2Na_2 \cdot H_2O$ | 55.33 / 55.22 | 7.48 / 7.55 | 4.16 / 4.16 | 649 |
| H | 230–241 (decompn) | $C_{29}H_{44}N_2O_6S_2Na_2 \cdot H_2O$ | 54.02 / 53.99 | 7.19 / 7.11 | 4.34 / 4.40 | 651 |
| I | 255–270 (decompn) | $C_{33}H_{52}N_2O_6S_2Na_2$ | 58.04 / 58.00 | 7.67 / 7.59 | 4.10 / 4.01 | 651 |
| J | 266–281 (decompn) | $C_{25}H_{36}N_2O_8S_2Na_2$ | 49.82 / 50.01 | 6.02 / 6.12 | 4.64 / 4.69 | 653 |
| K | 235–246 (decompn) | $C_{29}H_{44}N_2O_8S_2Na_2 \cdot H_2O$ | 51.46 / 51.66 | 6.85 / 6.78 | 4.13 / 4.12 | 650 |
| L | 233–250 (decompn) | $C_{27}H_{40}N_2O_8S_2Na_2$ | 51.41 / 51.22 | 6.39 / 6.42 | 4.44 / 4.44 | 649 |
| M | 277–288 (decompn) | $C_{31}H_{48}N_2O_8S_2Na_2$ | 54.21 / 54.00 | 7.04 / 7.11 | 4.07 / 4.04 | 648 |
| N | 270–282 (decompn) | $C_{35}H_{56}N_2O_6S_2Na_2 \cdot H_2O$ | 57.66 / 57.65 | 8.01 / 8.09 | 3.84 / 3.80 | 655 |
| O | 278–288 (decompn) | $C_{35}H_{56}N_2O_6S_2N_2$ | 59.13 / 59.12 | 7.93 / 7.95 | 3.94 / 3.92 | 654 |

By way of the following examples, the manufacturing method of the present invention compounds (Examples 1–3) and the method of quantitative determination using such compounds (Example 4) will be illustrated more specifically though the present invention is not limited to those examples so far as within a range of characteristic features of the present invention.

EXAMPLE 1

Manufacture of the Compound (F)

Sodium salt of N-ethyl-N-sulfopropyl-3,5-dimethylaniline (2.0 g) was dissolved in 12 ml of water, 0.31 ml of 37% formalin and 0.03 ml of 90% formic acid were added and the reaction was conducted by adding a catalytic amount of N-methylaniline keeping the mixture at 35° C. After conducting the reaction for 4 hours, the reaction solution was poured over 500 ml of acetone so that the crystals were isolated. The resulting crystals were collected by filtering and recrystallized from methanol to give 1.52 g of white methylenebis(N-ethyl-N-sulfopropyl-3,5-dimethylaniline sodium salt). The yield was 74.5%.

TLC (silica gel, n-butanol saturated with 0.2N aqueous ammonia): Rf=0.28

$^1$H-NMR (D$_2$O) δppM (TMC): 1.11 (t, J=7.1 Hz, 6H), 1.62–1.91 (m, 4H), 2.16 (s, 12H), 2.65 (t, 7.27, 4H), 3.48–3.74 (m, 8H), 4.22 (s, 2H), 7.17 (s, 4H).

IR (cm$^{-1}$): 3480, 1610, 1266, 1175.

EXAMPLE 2

Manufacture of the compound (L)

Sodium salt of N-ethyl-N-(2-hydroxy-3-sulfopropyl)-3,5-dimethylaniline (2.0 g) was dissolved in 10 ml of water, 0.30 ml of 37% formalin and 0.03 ml of 90% formic acid were added and, keeping the mixture at 35°–400° C., a catalytic amount of N-methylaniline was added thereto to conduct the reaction. After conducting the reaction for 4 hours, the reaction solution was poured over 500 ml of acetone to isolate the crystals. The resulting crystals were collected by filtering and recrystallized from methanol to give 1.52 g of white methylenebis[N-ethyl-N-(2-hydroxy-3-sulfopropyl)-3,5-dimethylaniline sodium salt]. The yield was 77.0%.

TLC (silica gel, n-butanol saturated with 0.2N aqueous ammonia): Rf=0.25

$^1$H-NMR (D$_2$O) δppM (TMS): 1.01 (t, J=6.6 Hz, 6H), 2.01 (s, 12H), 2.09–2.20 (m, 2H), 2.50 (d, J=2.1 Hz, 4H), 3.18–3.42 (m, 8H), 3.74 (s, 2H), 6.32 (s, 4H).

IR (cm$^{-1}$): 3500, 1603, 1220, 1160.

EXAMPLE 3

Manufacture of the Compound (O)

Sodium salt of N-butyl-N-sulfopropyl-3,5-diethylaniline (2.14 g) was dissolved in 20 ml of water, 0.31 ml of 37% formalin and 0.01 ml of 90% formic acid were added and, keeping the mixture at 35°–400° C., a catalytic amount of N-methylaniline was added thereto to conduct the reaction. After conducting the reaction for 4 hours, the reaction solution was poured over 500 ml of acetone to isolate the crystals. The resulting crystals were collected by filtering and recrystallized from methanol to give 1.46 g of white methylenebis(N-butyl-N-sulfopropyl-3,5-diethylaniline sodium salt). The yield was 67.1%.

TLC (silica gel, n-butanol saturated with 0.2N aqueous ammonia): Rf=0.34

$^1$H-NMR (D$_2$O) δppM (TMS): 0.97 (t, J=7.7 Hz, 6H), 1.20 (t, J=7.4 Hz, 12H), 1.39–1.68 (m, 8H), 1.55–1.76 (m, 4H), 2.66 (t, 7.6, 4H), 3.17–3.44 (m, 8H), 3.96 (s, 2H), 6.49 (s, 4H).

IR (cm$^{-1}$): 3380, 1600, 1239, 1212, 119, 1050.

EXAMPLE 4

Preparation of a Working Curve using Standard Hydrogen Peroxide Solution

Peroxidase (500 units) was dissolved in 100 ml of 50 mM MES [2-(N-morpholino)ethanesulfonic acid monohydrate] buffer (pH; 5.5). Four solutions were prepared and each of 5.43 mg of methylenebis(N-sulfopropyl-3,5-dimethylaniline disodium salt) (Compound B), 5.98 mg of methylenebis(N-ethyl-N-sulfopropyl-3,5dimethylaniline disodium salt) (Compound F), 6.83 mg of methylenebis(N-propyl-N-sulfopropyl-3,5-diethylaniline disodium salt) (Compound I) and 6.31 mg of methylenebis[N-ethyl-N-(2-hydroxy-3-sulfopropyl)-3,5-dimethylaniline disodium salt] (Compound L) was dissolved in each of the solution to prepare four coloring reagents.

To each of the coloring reagents were assigned test tubes a–f and each of the test tubes was filled with the coloring reagent and standard hydrogen peroxide solution as follows.

| | Standard H$_2$O$_2$ Solution | Coloring Reagent |
|---|---|---|
| a | 0.05 mM (10 μl) | 1.0 ml |
| b | 0.10 mM (10 μl) | 1.0 ml |
| c | 0.20 mM (10 μl) | 1.0 ml |
| d | 0.50 mM (10 μl) | 1.0 ml |
| e | 1.00 mM (10 μl) | 1.0 ml |
| f | 2.00 mM (10 μl) | 1.0 ml |

Each test tube was dipped in a thermostat of 37° C. for 10 minutes and extinction at maximum absorption wavelength for each one was measured using the blank reagent as a control. The working curve prepared from the measured result is given in FIG. 1. It is clear from FIG. 1 that the working curves for all coloring reagents exhibit linearity within a concentration range of 1–100 μM. Out of the above result, it is clear that all of the present invention compounds are effective as reagents for quantitative determination of peroxides. Specific example for quantitative determination will be given as hereunder for the Compound F which showed the highest sensitivity in the above measurements. It is, however, to be understood that this is mere exemplification and that the present invention is not limited thereto.

EXAMPLE 5

Quantitative Determination of Glucose in Serum using the Compound F

Glucoseoxidase (500 units), 500 units of peroxidase and 5.98 mg of methylenebis(N-ethyl-N-sulfopropyl-3,5-dimethylaniline disodium salt) (Compound F) were dissolved in 100 ml of 50mM MES buffer (pH: 5.5) to prepare a coloring reagent.

i) Preparation of working curve using standard glucose solution.

Glucose (200 mg) was dissolved in 100 ml of water to prepare a standard glucose solution. This was diluted to desired extent and used for the experiments.

Reagents were placed in the test tubes a–d as follows:

| | Standard Glucose Solution | | Coloring Reagent |
|---|---|---|---|
| a | Diluted to ¼ | 20 ml | 1.0 ml |
| b | Diluted to ½ | 20 ml | 1.0 ml |
| c | Diluted to ¾ | 20 ml | 1.0 ml |
| d | Not diluted | 20 ml | 1.0 ml |

Each of the test tubes was dipped in a thermostat of 37° C. for 10 minutes and the extinction at 648 nm was measured using the blank test as a control. The working curve prepared from the measured values is given in FIG. 2. The result shows that good linearity is available within a glucose concentration range of 0–200 mg/dl.

ii) Quantitative determination of glucose in serum.

Deproteinized serum (20 ml) was placed in a test tube, 1.0 ml of the above coloring reagent was added, the mixture was dipped in a thermostat of 37° C. for 10 minutes, the extinction at 648 nm was measured using the blank test as a control and glucose concentration in the serum was determinted by comparing with the working curve.

Sample I (male; age: 32)
  Extinction: 0.293
  Glucose concentration: 91.69 mg/dl Sample II (male; age: 28)
    Extinction: 0.333
    Glucose concentration; 105.24 mg/dl
Sample III (male; age: 36)
    Extinction: 0.361
    Glucose concentration: 112.98 mg/dl

Figure 1:
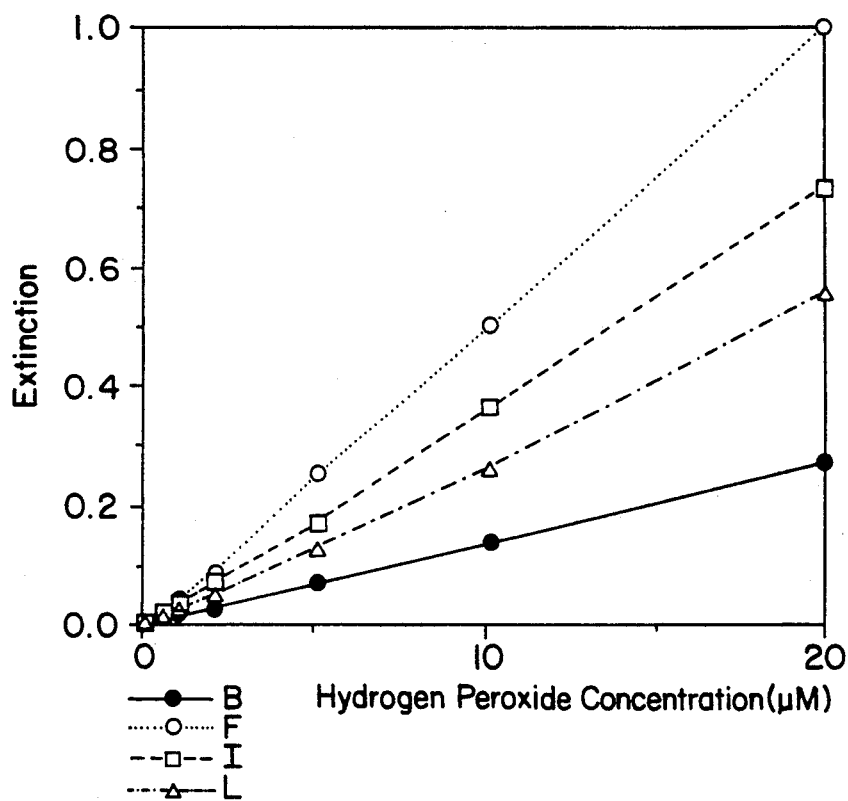
FIG. 1 shows working curves of the reagents B, F, I and L against hydrogen peroxide concentration in which ordinate shows the extinctin at maximum absorption wavelength while abscissa shows the hydrogen peroxide concentration and •, ○, □ and Δ correspond to the Compounds B, F, I and L, respectively.
Figure 2:
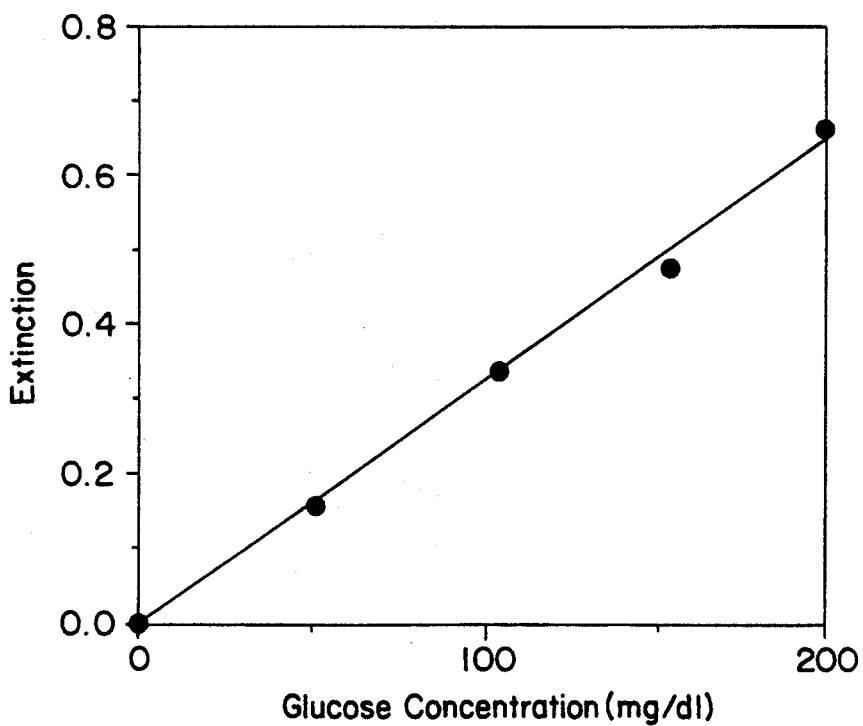
FIG. 2 shows working curve for glucose when the reagent F is used wherein ordinate shows the extinction at 648 nm while abscissa shows the glucose concentration.

We claim:

1. Water-soluble methylenebis(dialkylaniline) derivative represented by the general formula

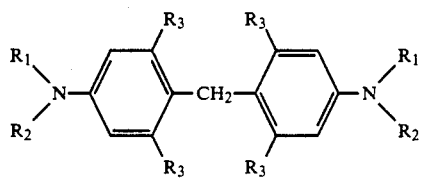

(wherein $R_1$ is hydrogen or a substituent selected from a group consisting of lower alkyl and $C_{2-3}$ sulfoalkyl or hydroxysulfoalkyl; $R_2$ is $C_{2-3}$ sulfoalkyl or hydroxysulfoalkyl; and $R_3$ is lower alkyl) and salt thereof.

2. The compound according to claim 1, which is methylene-bis (N-ethyl-N-sulfopropyl-3,5-dimethylaniline).

3. The compound according to claim 1, which is methylene-bis[N-ethyl-N-(2-hydroxy-3-sulfopropyl)-3,5-dimethylaniline].

4. A composition useful for the quantitative determination of peroxides in a biological system which comprises a biologically effective amount of a water-soluble derivative of the formula (1)

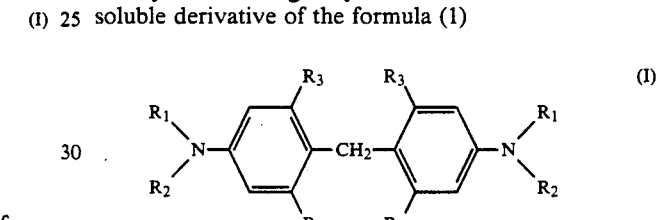

or a salt thereof as a dye-forming substance wherein $R_1$ is hydrogen or a substituent selected from a group consisting of lower alkyl and $C_{2-3}$ sulfoalkyl or hydroxysulfoalkyl; $R_2$ is $C_{2-3}$ sulfoalkyl or hydroxysulfoalkyl; and $R_3$ is lower alkyl in combination with an inert diluent or carrier.

5. The composition according to claim 4 wherein the compound is methylenebis(N-ethyl-N-sulfopropyl-3,5-dimethylaniline).

6. The composition according to claim 4 wherein the compound is methylene-bis[N-ethyl-N-(2-hydroxy-3-sulfopropyl-3,5-dimethylaniline].

7. A method for quantitative determination of peroxides in a biological system which comprises applying to said system a biologically effective amount of a water-soluble derivative of the formula (1)

(I)

or a salt thereof as a dye-forming substance wherein $R_1$ is hydrogen or a substituent selected from a group consisting of lower alkyl and $C_{2-3}$ sulfoalkyl or hydroxysulfoalkyl; $R_2$ is $C_{2-3}$ sulfoalkyl or hydroxysulfoalkyl; and $R_3$ is lower alkyl in combination with an inert diluent or carrier.

8. The method according to claim 7 wherein the compound is methylene-bis(N-ethyl-N-sulfopropyl-3,5-dimethylaniline).

9. The method according to claim 7 wherein the compound is methylene-bis[N-ethyl-N-(2-hydroxy-3-sulfopropyl)-3,5-dimethylaniline].

* * * * *